United States Patent [19]

Tsuchihashi et al.

[11] Patent Number: 4,539,420
[45] Date of Patent: Sep. 3, 1985

[54] OPTICALLY ACTIVE 1-AROMATIC-GROUP-SUBSTITUTED-1-ALKANONES AND METHODS FOR THEIR MANUFACTURE

[75] Inventors: Gen-Ichi Tsuchihashi, Tokyo; Shuichi Mitamura; Koji Kitajima, both of Kanagawa, all of Japan

[73] Assignee: Syntex Pharmaceuticals International Limited, Hamilton, Bermuda

[21] Appl. No.: 387,585

[22] Filed: Jun. 11, 1982

[30] Foreign Application Priority Data

Jun. 15, 1985 [JP] Japan ........................................ 90978

[51] Int. Cl.$^3$ .............................................. C07C 69/76
[52] U.S. Cl. .................... 560/056; 560/100; 560/105; 560/9; 260/456 R; 556/441; 568/323; 568/591
[58] Field of Search ....................... 560/100, 105, 56, 9

[56] References Cited

FOREIGN PATENT DOCUMENTS 53-3012837   4/1978   Japan .................................... 560/105

*Primary Examiner*—Paul J. Killos
*Attorney, Agent, or Firm*—John A. Dhuey; Joseph I. Hirsch

[57] ABSTRACT

A manufacturing method is described for the preparation of optically active 1-aromatic-group-substituted-1-alkanones characterized in that an optically active alkane acid halide is allowed to react with an aromatic compound in the presence of a Lewis acid. The optically active 1-aromatic-group-substituted-1-alkanones are useful intermediates in the preparation of optically active alpha-arylalkanoic acids, which are useful as pharmaceutical, e.g. anti-inflammatory, analgesic and anti-pyretic, agents and as insecticidal agents.

8 Claims, No Drawings

OPTICALLY ACTIVE 1-AROMATIC-GROUP-SUBSTITUTED-1-ALKANONES AND METHODS FOR THEIR MANUFACTURE

BACKGROUND OF THE INVENTION

1. Field of the Invention

The present invention relates to a process for preparing pharmaceutically and agriculturally useful optically active alpha-arylalkanoic acids, esters and pharmaceutically acceptable salts thereof. More specifically, it is concerned with a method of producing optically active intermediates which are useful in preparing the optically active alpha-arylalkanoic acids, esters and pharmaceutically acceptable salts referred to above.

1. State of the Art

Numerous alpha-arylalkanoic acids (i.e. 2-arylalkanoic acids have been described, developed and found to be useful as pharmaceutical and agricultural agents. Specific compounds have been described in U.S. Pat. Nos. 3,385,386; 3,600,437; 3,624,142; 3,755,427; 3,904,682; and 3,912,748. Process for manufacturing those types of compounds have been described previously in U.S. Pat. Nos. 4,135,051; 3,975,431; 3,658,863; 3,663,584; 3,658,858; 3,694,476; and 3,959,364. More recently, various processes have been described in U.K. Patent Publication No. 2,042,543, published Sept. 24, 1980 (corresponding to U.K. application No. 8005752, filed Feb. 20, 1980); in European Patent Publication No. 0034871, published Sept. 2, 1981 (corresponding to European patent Application No. 81200210.3, filed Feb. 23, 1981); and in Tetrahedron Letters, Vol. 22, No. 43, pp. 4305-4308 (1981).

SUMMARY OF THE INVENTION

The present invention relates to a manufacturing method for preparing optically active 1-aromatic-group-substituted-1-alkanones expressed by the general formula

characterized in that optically active halides of alkane acids expressed by the general formula

are reacted with aromatic compounds expressed by the general formula

Ar—H in the presence of a Lewis acid. [In the above formulas, Ar is an aromatic group, R is a saturated aliphatic group, X is a halogen atom or a sulfonyloxy group, and Y is a halogen, e.g. chlorine or bromine, atom. * indicates an asymmetric carbon atom.] The optically active 1-aromatic-group-substituted 1-alkanones are useful intermediates in the preparation of alpha-arylalkanoic acids, esters and pharmaceutically acceptable salts thereof, which are useful as pharmaceutical, e.g. anti-inflammatory, analgesic and anti-pyretic, agents and as insecticidal agents.

Also comprehended within the present invention are the optically active acetals of the 1-aromatic-group-substituted-1-alkanones expressed by the general formula

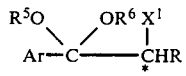

wherein Ar and R are as defined above, $R^5$ and $R^6$ are alkyl, optionally the same or different, or, when taken together, are alkylene having 2-8 carbon atoms, and $X^1$ is hydroxy, a halogen atom or a sulfonyloxy group.

DETAILED DESCRIPTION OF THE INVENTION

This invention relates to optically active 1-aromatic-group-substituted-1-alkanones expressed by the general formula

[Here, Ar is an aromatic group, R is an alkyl or cycloalkyl group, and X is a halogen atom or a sulfonyloxy group. * indicates an asymmetric carbon atom.] and acetals thereof.

Ar is an aromatic group in the aforesaid general formula (I). The term "aromatic group", as used in the present specification and appended claims, is to be taken in its broadest meaning, and denotes a group of a cyclic compound having aromaticity. The aromaticity means a phenomenon wherein the ring is stabilized by the delocalization of π electrons. Generally, a ring having (4n+2) conjugated π electrons is stable and exhibits aromaticity. Thus, the aromatic group, as used herein, refers to a group of compounds having (4n+2) conjugated π electrons in the main ring. It can be classified roughly into aryl groups optionally having at least one substituent and heteroaromatic groups optionally having at least one substitutent, which are described in detail below.

(a) Aryl groups optionally having at least one substituent.

The aryl groups are aromatic hydrocarbon groups having from 6 to 20 carbon atoms of the monocyclic, polycyclic or condensed polycyclic type, and include, for example, phenyl, biphenyl and naphthyl.

The aryl groups may be unsubstituted, or have one or more substituents on the aromatic ring. Specific examples of the substituents include halogen atoms such as chlorine, bromine, fluorine, and iodine; lower alkyl groups such as methyl, ethyl, n-propyl, isopropyl, n-butyl, isobutyl, and tert-butyl; cycloalkyl groups such as cyclohexyl and cyclopentyl; aralkyl groups such as benzyl; lower alkoxy groups such as methoxy, ethoxy, n-propoxy and isopropoxy; lower alkylthio groups such as methylthio, ethylthio, n-propylthio, isopropylthio, and butylthio; arylthio groups such as phenylthio, tolylthio, and naphthylthio; alkenylthio groups such as alkylthio; aralkylthio such as benzylthio; acyloxy groups such as acetoxy; aroyloxy groups such as benzoyloxy; silyloxy groups such as trimethylsilyloxy; lower alkenyl groups such as allyl and prenyl [$(CH_3)_2C=CH—CH_2—$]; lower alkenyloxy groups such as allyloxy; aralkyloxy groups such as benzyloxy and phenethyloxy; aryloxy groups such as phenoxy; lower haloalkyl groups such as trifluoroethyl and trifluoropropyl; lower haloalkoxy groups such as difluoromethoxy and trifluoromethoxy; 4- to 6-membered heterocyclic groups such as indolinyl, oxo-isoindolynyl thienyl, piperidino and phthalimido; 4- to 6-membered heterocycloxy groups such as thiazoyloxy, and pyridyloxy; a nitro group; aroyl groups such as benzoyl; acylamino groups such as acetylamino and propionylamino; aroylamino groups such as benzolyamino; and dialkylamino groups such as kimethylamino and dibenzylamino. When these substituents are present, 1 to 5, preferably 1 to 3, of them are preferably present on the aromatic ring.

Specific examples of aryl groups having such substituents on the aromatic ring include chlorophenyl, fluorophenyl, bromophenyl, iodophenyl, tolyl, ethylphenyl, isopropylphenyl, tert-butylphenyl, cyclohexylphenyl, methoxyphenyl, ethoxyphenyl, isopropoxyphenyl, methylthiophenyl, ethylthiophenyl, n-propylthiophenyl, isopropylthiophenyl, butylthiophenyl, phenylthiophenyl, tolylthiophenyl, allylthiophenyl, benzylthiophenyl, acetoxyphenyl, trimethylsilyloxyphenyl, benzoyloxyphenyl, benzylphenyl, prenylphenyl, allyloxyphenyl, benzyloxyphenyl phenoxyphenyl, tetrafluoroethoxyphenyl, trifluoroethylphenyl, trifluoromethoxyphenyl, difluoromethoxyphenyl, oxo-isoindolinylphenyl, thioazolyloxyphenyl, nitrophenyl, benzoylphenyl, acetylaminophenyl, piperidinophenyl, fluorobiphenyl, acetylaminobiphenyl, and methoxynaphthyl, methylthienylphenyl, acetylamino-chloro-phenyl-chloro-cyclohexyl-phenyl.

(b) Heteroaromatic groups optionally having at least one substituent.

The heteroaromatic group may be of any of the monocyclic or condensed polycyclic type. The heteroatom of the heteroaromatic ring may be nitrogen, oxygen or sulfur. The heteroaromatic ring contains generally 1 to 4, preferably 1 to 3, such hetero atoms, and may be generally 5- or 14-membered, preferably 5- to 9-membered. Specific examples of such heteroaromatic groups are thienyl, furyl, pyrolyl, indolyl, phenothiazinyl, pyridyl, thiazolyl, and benzothiazolyl.

The heteroaromatic group may be unsubstituted, or may contain one or more substituents on the ring. Examples of substituents which may be present on the heterocyclic aromatic ring are lower alkyl groups such as methyl, ethyl, propyl and butyl; aryl groups such as phenyl and fluorophenyl; halogen atoms such as chlorine and fluorine; lower alkoxy groups such as methoxy, ethoxy and propoxy; aryloxyl groups such as a phenoxy lower alkyl groups such as methyl, ethyl, propyl, and butyl; aralkyl groups such as benzyl; aryl groups such as phenyl, tolyl, and fluorophenyl; halogen atoms such as fluorine, chlorine and bromine; lower alkoxy groups such as methoxy, ethoxy, and propoxy; cycloalkyl groups such as cyclohexyl and cyclopentyl; lower alkenyl groups such as allyl and prenyl; lower alkenyloxy groups such as allkyloxy; aralkyloxy groups such as benzyloxy; aryloxy groups such as phenoxy; lower haloalkyl groups such as trifluoromethyl; lower alkylthio groups such as methylthio; arylthio groups such as phenylthio; aroyl groups such as benzoyl, toluoyl, and chlorobenzoyl; acyl groups such as acetyl; lower haloalkyl groups such as trifluoromethyl; and cycloalkyl groups such as cyclohexyl.

When these substituents are present, 1 to 8, preferably 1 to 3, of them are desirably present.

Thus, examples of heteroaromatic groups having such substituents include methylphenothiazinyl, methoxymethyl-phenothiazinyl, methylpyrrolyl, toluoyl-methylpyrrolyl, phenylthienyl, bromothienyl, trifluoromethylthienyl, benzoylthienyl, cyclohexylthienyl, phenoxythienyl, methyl-methoxy-indolyl, chlorobenzoyl-indolyl, acetylpyrrolyl, methyl-toluoyl-pyrrolyl, benzylpyrrolyl.

As presently preferred examples of such aromatic groups, one may mention the phenyl group; halophenyl groups such as fluorophenyl, chlorophenyl, bromophenyl, and iodophenyl; alkenylphenyl groups such as 4-isobutylpheyl, 4-t-butylphenyl or 4-prenylphenyl; alkoxyphenyl groups such as alkylphenyl, methoxyphenyl, ethoxyphenyl, isopropoxyphenyl, benzyloxyphenyl or allyloxyphenyl; aromatic-group-substituted oxyphenyl groups such as alkenyloxyphenyl, phenoxyphenyl or thiazolyloxyphenyl; substituted aminophenyl groups such as acetylaminophenyl, isoindolylphenyl or methanesulfonyl aminophenyl; biphenyl groups such as 4-biphenylyl, fluorobiphenylyl or acetylaminobiphenylyl; complex aromatic groups such as thienyl, furyl, indolyl or phenothiazinyl; and condensation polycyclic aromatic groups such as 6-methoxy-2-naphthyl.

R is a saturated aliphatic group. The term "saturated aliphatic group", as used in the present specification and the appended claims, denotes a linear, branched, or cyclic saturated aliphatic hydrocarbon group which may generally contain 1 to 10 carbon atoms, preferably 1 to 6 carbon atoms. Examples of such saturated aliphatic groups include linear or branched alkyl groups having 1 to 6 carbon atoms, especially lower alkyl groups, such as methyl, ethyl, n-propyl, isopropyl, n-butyl, isobutyl, tert-butyl, n-pentyl, isoamyl, and n-hexyl, and cycloalkyl groups having 3 to 10 carbon atoms, especially cycloalkyl groups having 3 to 7 carbon atoms, such as cyclopropyl, cyclopentyl, cyclohexyl, cycloheptyl. As preferred examples of the alkyl groups, one may mention methyl, ethyl, propyl, isopropyl, butyl and pentyl; and as examples of the cycloalkyl groups one may mention cyclopropyl and cyclohexyl.

X is a halogen atom (i.e. bromine, chlorine or iodine) or a sulfonyloxy group. The preferred sulfonyloxy groups can be represented by the general formula

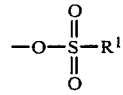

wherein $R^1$ is a saturated aliphatic group as defined above, a substituted alkyl group including a substituted lower alkyl group) or a substituted or unsubstituted aromatic group (including substituted or unsubstituted phenyl groups of the formula

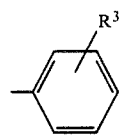

wherein $R^3$ represents a hydrogen atom, a halogen atom, a nitro group or a lower alkyl group). Examples of the substituents which may be present on the alkyl group in the "substituted alkyl group" are halogen atoms such as chlorine, bromine and fluorine; aryl groups such as phenyl; alkoxy groups such as methoxy and ethoxy; and alicyclic groups such as [1R, 4R] or [1S, 4S]-7,7-=dimethyl-2-oxobicyclo[2,2,1]heptan-1-yl. Specific examples of such substituted alkyl groups include trifluoromethyl, d- or -10-camphoryl, and benzyl. As preferred examples of the sulfonyloxy groups, one may mention saturated aliphatic-group-substituted sulfonyloxy groups such as methanesulfonyloxy, ethanesulfonyloxy, butanesulfonyloxy and trifluoromethanesulfonyloxy; aromatic-group-substituted sulfonyloxy groups such as benzenesulfonyloxy, para-toluenesulfonyloxy, para-bromobenzenesulfonyloxy and para-nitrobenzene-sulfonyloxy; as well as halosulfonyloxy groups such as fluorosulfonyloxy.

The "alkyl group" and "alkylene group", used in the present specification and appended claims, may be any one of linear or branched types, and the alkylene groups are preferably lower alkylene groups such as ethylene propylene, butylene, trimethylene, or tetramethylene.

The term "lower", as used in the present specification and appended claims to qualify a group or a compound means that the group or compound so qualified has not more than 6, preferably not more than 4, carbon atoms.

The optically active 1-aromatic-group-substituted-1-alkanones expressed by the aforesaid general formula (I) are novel compounds which have a hitherto unknown manufacturing method, and they serve as important intermediates in the manufacturing of various optically active compounds. For example, optically active substances which are expressed by the aforesaid general formula (I) in which X is the sulfonyloxy group may be reacted with alkali metal alkoxides in an alcohol to derive an optically active 1-aromatic-group-substituted-2-hydroxy-1-alkanone acetal, which is next subjected to the action of an 0-sulfonylating agent, such as methanesulfonyl chloride, in order to obtain an optically active 1-aromatic-group-substituted-2-sulfonyloxy-1-alkanone acetal. When this is then subjected to a rearrangement reaction, as described more fully below, one can derive with a good yield the optically active alpha-aromatic-group-substituted alkane acids, expressed by the general formula

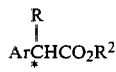
ArCHCO$_2$R$^2$ (II)

(Ar and R are the same as defined above, and R$^2$ is a hydrogen atom, an alkyl group or a hydroxyalkyl group) or the pharmaceutically acceptable salts, e.g. the sodium salt, thereof, which salts are obtained by methods known per se.

Among the optically active compounds expressed by the aforesaid general formula (II) there are some, such as (+)-alpha(4-difluoromethoxyphenyl)isovaleric acid or (+)-alpha-(6-methoxy-2-naphthyl)propionic acid, which are far more effective as raw materials for agricultural chemicals or as pharmaceutical drugs than their corresponding racemic modifications. The optically active alpha-aromatic-group-substituted alkane acids expressed by the aforesaid general formula (II) were manufactured in the past by optical resolution of their corresponding racemic modifications. For example, a method has been proposed for obtaining (+)-alpha-(6-methoxy-2-naphthyl)propionic acid by optical resolution of the corresponding racemic modification, using cinchonidine as the resolving agent (Japanese Patent Application Publication No. 14097-1981). Furthermore, the method utilizing optical resolution of the racemic modifications is economically disadvantageous because the other optical isomers, which amount to half of the contents of the racemic modifications, are not needed. A cumbersome process of racemization is necessary in order to reutilize these other optical isomers. In addition, expensive resolving agents are usually necessary. On the other hand, optical resolution is not needed in the method using as the raw materials the optically active compounds expressed by the aforesaid general formula (I), which can be manufactured cheaply and easily by the method of this invention. Consequently this method is considerably more advantageous from the economical viewpoint than the conventional methods of the past. Moreover, many optically active useful compounds can be manufactured by using the optically active compounds expressed by the aforesaid general formula (I) in which X is a chlorine or bromine atom as the raw materials for reactions which are already widely known in the form of racemic modifications corresponding to (I).

Even though the optically active 1-aromatic-group-substituted-1-alkanones expressed by the aforesaid general formula (I) are compounds which can be important intermediates in the manufacturing of various optically active compounds, methods for manufacturing them were not yet known. However, as a result of this invention, the optically active compounds expressed by the aforesaid general formula (I) can be manufactured with a good yield by the method herein described, using inexpensive and easily available optically active compounds as the raw materials.

In this invention, optically active halides of alkane acids expressed by the general formula

(III)

(R and X are the same as defined above, and Y is a halogen atom, preferably a chlorine or bromine atom) and aromatic compounds expressed by the general formula

Ar—H (IV)

(Ar is the same as defined above) are condensed by the so-called Friedel-Crafts reaction in the presence of a Lewis acid, and optically active compounds expressed by the aforesaid general formula (I) are obtained.

In Friedel-Crafts reactions between optically active halides of alkane acids, the optical activity of which originates in asymmetric carbon in the 2-position, and aromatic compounds, it has been reported in the past that in cases where the carbon in the 2-position is a secondary carbon, as in the case of phenyl-paratolylacetyl chloride, the 1-aromatic-group-substituted-1-alkanones, which are the products, lose their optical activity originating in the asymmetric carbon in the 2-position, and the products become racemic modifications. (See H. Hart, *Friedel Crafts and related reactions*, ed. G. A. Olah, vol. 1, pp. 1009–1010, Interscience Publishers, New York and London, 1963 and W. Bleazard, E. Rothstein, *J. Chem. Soc.*, 3789 (1958).) Nevertheless, it has been discovered that when optically active halides of alkane acids expressed by the aforesaid general formula (III) are used, almost no racemic modifications are produced by Friedel-Crafts reactions with aromatic compounds expressed by the aforesaid general formula (VI), and optically active 1-aromatic-group-substituted-1-alkanones expressed by the aforesaid general formula (I) are obtained in almost optically pure form.

The optically active halides of alkane acids expressed by the aforesaid general formula (III), which are the raw material compounds for this invention, can be manufactured from inexpensive and easily available optically active lactic acid (VI: R=CH$_3$) or optically active alpha-amino acid (V), for example by following the reaction sequence given below. Moreover, each of the processes can be carried out without lowering the optical purity.

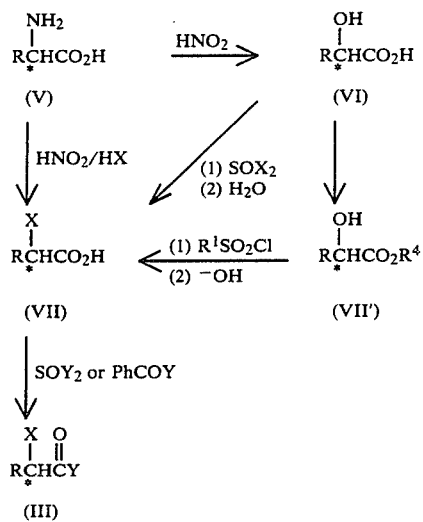

(Here, R, R$^1$, X and Y are the same as defined above and R$^4$ is lower alkyl).

The target compounds can be manufactured by reacting the optically active halides of alkane acids expressed by the aforesaid general formula (III), which can be manufactured easily in this way, and an approximately equimolar amount of the aromatic compounds expressed by the aforesaid general formula (IV) in the presence of a Lewis acid. Representative Lewis acids are the organic salts, such as acetate, propionate, benzoate, trifluoromethanesulfonate, methanesulfonate, and the like, and the inorganic salts such as chloride, bromide, iodide, sulfate, oxide and the like of aluminum, copper, magnesium, calcium, zinc, cadmium, barium, mercury, tin, antimony, bismuth, manganese, iron, cobalt, nickel and palladium, and borontrifluoride and the like. The metal halides such as aluminum chloride, zinc chloride, cobalt chloride, zinc bromide, stannous chloride, ferrous chloride, ferric chloride, nickel bromide, cadmium chloride, magnesium chloride, mercurous chloride, mercuric chloride, antimony chloride, barium chloride, calcium chloride, cuprous chloride, cupric chloride, manganese chloride, stannic chloride, bismuth chloride and palladium trichloride are considered particularly useful. The Lewis acids which are especially suitable for use are aluminum chloride, aluminum bromide, stannic chloride, ferrous chloride, zinc chloride, and trifluoroboron.

In cases where the X in the raw material compounds (III) is a sulfonyloxy group, the use of a relatively weak Lewis acid, is one of low acidity, such as ferrous chloride, ferric sulfate magnesium bromide and zinc chloride, especially ferric sulfate and ferrous chloride, is presently preferred. As for the amount of Lewis acid to be used, usually an equimolar amount with the amount of the raw material compound (III) is sufficient. However, when the aromatic compound (IV) has functional group which coordinates easily with the Lewis acid, such as acetanilide, good results can be brought about by using excessive quantities as necessary. When implementing the method of this invention, it is desirable to carry out the reaction in a solvent. As the solvents, a broad range of compounds which are used in ordinary Friedel-Crafts reactions can be used, such as carbon disulfide, 1,2-dichloroethane, petroleum ether, hexane, nitramethane or nitrobenzene. However, when a compound in which X is sulfonyloxy group is used as the raw material in the aforesaid general formula (III), it is desirable to use as the solvent a compound with a relatively high degree of polarity, such as nitromethane or nitrobenzene.

The reaction proceeds ordinarily at temperatures ranging from −10° C. to 100° C., but it is desirable to carry it out within a temperature range of 0°–50° C. in order to obtain the target substances rapidly. After the reaction, water can be added to the reaction mixture, and then the product can be obtained by procedures such as extraction with an organic solvent, in the same way as in an ordinary Friedel-Crafts reaction. In this matter, it is possible to obtain with a good yield the target compounds expressed by the aforesaid general formula (I) in more or less optically pure form.

The optically active intermediates of formula (I) are further transformed as described below. An alkali metal alkoxide is allowed to react with the compound of general formula (I) in the presence of the corresponding alcohol to give the corresponding alpha-hydroxyketone acetal. Lithium alkoxides, sodium alkoxides and potassium alkoxides can be suitably used as the alkali metal alkoxide. The use of the sodium alkoxides is preferred because of their low cost. The amount of the alkali metal alkoxide is generally at least 1 mole per mole of the compound of formula (I), and the reaction can be completed rapidly if it is used in an amount of 1.5 to 3 moles per mole of the compound of formula (I). The amount of the alcohol to be copresent may be at least 1 mole per mole of the compound of general formula (I). Advantageously, the alcohol is used in excess to make it serve also as a solvent. It is also possible to add an aprotic solvent which does not participate in the reaction, such as diethyl ether, tetrahydrofuran, DMF, or 1,2-dimethoxyethane. The reaction proceeds smoothly at a temperature of about −20° C. to about 100° C. For the simplicity of the operation, the reaction is preferably carried out at room temperature to 60° C.

According to another embodiment, this step can be performed by reacting the compound of formula (I) with the alkali metal alkoxide in a aprotic solvent such as diethyl ether, tetrahydrofuran or 1,2-dimethoxyethane to form an epoxy compound, and then reacting it with, an alcohol in the presence of a catalytic amount of an alkali metal alkoxide to obtain an alpha-hydroxyketone acetal.

The reaction between the compound of formula (I) and the alkali metal alkoxide can be carried out usually at a temperature of about 0° C. to about 60° C. using 1 to 3 moles, per mole of the compound of formula (I), of the alkali metal alkoxide. The reaction between the epoxidized compound and the alcohol can be performed generally at a temperature of about 0° C. to about 100° C. by using at least one mole, per mole of the epoxidized compound, of the alcohol. Preferably the alcohol is used in excess to make it serve also as a solvent.

Equivalently, the cyclic acetals can be formed with the use of glycols and other polyhydric alcohols (e.g. those having from 2–8 carbon atoms) such as ethylene glycol, trimethylene glycol, dimethylpropylene glycol and the like, according to conventional methods.

The next step involves the action of an O-sulfonylating agent of the formula $R^4-SO_2-Hal$ or $(R^4SO_2)_2O$ on the alpha-hydroxyketone acetal obtained in the above step to form the alpha-sulfonyloxyketone acetal.

Examples of the O-sulfonylating agent include aromatic group substituted sulfonyl halides such as benzenesulfonyl chloride, p-toluenesulfonyl chloride, p-bromobenzenesfulfonyl chloride, p-nitrobenzenesulfonyl chloride and naphthalene sulfonyl chloride; and alkanesulfonyl halides or alkanesulfonic anhydrides, such as methanesulfonyl chloride, butanesulfonyl chloride, methanesulfonic anhydride, trifluoromethanesulfonic anhydride, trifluoromethanesulfonyl chloride, d-10-camphorsulfonyl chloride, and l-10-camphorsulfonyl chloride.

The reaction is desirably carried out under neutral to basic conditions, and from this standpoint, the reaction is advantageously carried out in the presence of at least 1 mole, per mole of the alpha-hydroxyketone acetal, of a tertiary amine such as triethylamine, pyridine, or 4-dimethylaminopyridine. In this way, the reaction can be performed at a relatively low temperature or from about 0° C. to room temperature. It is also possible to add an aprotic solvent which does not participate in the reaction, such as methylene chloride or diethyl ether.

The alpha-sulfonyloxyketone acetal derived above is then rearranged to form the compound of formula (II) such as by contacting with a protic or dipolar, aprotic solvent or by hydrolysis.

When the specified acetal compound having a sulfonyloxy group at the 2-position and an aromatic group (Ar) at the 1-position is hydrolyzed, a reaction takes place in which the sulfonyloxy group is split off and the aromatic group is shifted to the 2-position to give an alpha-aromatic group substituted alkanoic acid of general formula (II).

The hydrolysis reaction may be carried out in the absence of a solvent. Desirably, however, it is carried out generally in an inert solvent. Examples of the inert solvent are aprotic polar solvents such as dimethyl formamide (DMF), dimethyl sulfoxide (DMSO), 1,3-dimethyl-2-imidazolidinone (DMI), 1,4-dioxane, tetrahydrofuran (THF) diethylene glycol dimethyl ether (diglyme), hexamethylphosphoric triamide (HMPA), 1,2-dimethoxyethane, and pyridino; and protic polar solvents such as methanol, ethanol, ethylene glycol, and acetic acid. These solvents may be used solely or as a mixture of two or more. Alternatively, the rearrangement can proceed in the absence of water, but in a protic or dipolar, aprotic solvent.

The reaction temperature is not critical, and can be varied widely according to the type of the starting material. Generally, temperatures between about 0° C. and about 250° C., preferably room temperature to about 200° C., can be used. In order to promote the reaction, the reaction is conveniently carried out at an elevated temperature, preferably from about 40° C. to the refluxing temperature of the reaction mixture, more preferably from about 50° C. to about 180° C. The reaction may be carried out at atmospheric or elevated pressures.

Water required for hydrolysis may be incorporated in advance in a solvent of the type exemplified hereinabove and the compound may be mixed in the solvent to perform the reaction. Alternatively, it is possible to mix the compound in the solvent, add water to the mixture, and react the water with the compound.

Alternatively, the compound is heated to a temperature within the above range in an above solvent under anhydrous conditions, and then water is added to hydrolyze the compound.

From the standpoint of the ease of operation, it is convenient to introduce the compound into a mixture of water and an above polar solvent.

The amount of water required for hydrolysis is not critical, and can be varied widely depending upon the type of the compound used, the reaction conditions, etc. Generally, it is used in an amount of at least 1 mole, preferably at least 5 moles, per mole of the compound. If it is used in too large an amount, the solubility of the compound decreases. Hence, it is preferable not to use water in too excessive an amount.

In order to prevent the undesired cleavage of the acetal moiety of the compound by an acid, the hydrolysis is preferably carried out generally under neutral or basic (pH about 7–14) conditions.

Since the sulfonyloxy group at the 2-position is split off as sulfonic acid in the hydrolysis reaction, it is convenient to cause a base to be present in the reaction system in order to maintain the reaction system under neutral to basic conditions during the proceeding of the reaction. Examples of the base which can be used for this purpose include alkali metal hydroxides such as potassium hydroxide and sodium hydroxide; alkaline earth metal hydroxides such as magnesium hydroxide and calcium hydroxide; alkali metal carbonates such as potassium carbonate and sodium carbonate; alkaline earth metal carbonates such as magnesium and calcium carbonate; alkali metal bicarbonates such as potassium and sodium bicarbonate; alkali metal carboxylates such as sodium formate, sodium acetate, potassium acetate and sodium propionate; alkalimetal phosphates such as sodium and potassium phosphate; and organic tertiary amines such as pyridine, triethylamine, and tributylamine. These inorganic or organic bases are conveniently used in an amount of generally at least 1 equivalent, preferably 1 to 10 equivalents, per mole of the compound of formula (II).

The hydrolysis reaction can be terminated generally within about 1 to about 250 hours although this depends upon the type of the starting compound and the reacton conditions.

In the above hydrolysis reaction, the sulfonyloxy group at the 2-position of the compound is split off, and the aromatic group (Ar) at the 1-position is shifted to the 2-position. At the same time, either one of the acetal groups is split off, and the remaining one acetal group forms the group $-OR^2$ in the compound of formula (II) (in which $R^2$ is an alkyl group). Depending upon the conditions used in the hydrolysis, especially under strongly basic conditions, the ester formed [the compound of formula (II) in which $R^2$ is an alkyl group] further undergoes hydrolysis to form the compound of formula (II) in which R[2] is a hydrogen atom. When a cyclic acetal is employed as the substrate for hydrolysis, a corresponding compound of formula (II) in which R[2] is a hydroxylakyl is obtained.

The invention is further illustrated by the embodiments described in the following illustrative examples. While the invention is described with reference to those specific embodiments, it is understood that various changes and modifications can be made, and equivalents substituted, by those skilled in the art without departing from the spirit and scope of the invention. All such modifications, changes and substitutions are intended to be within the scope of the claims appended hereto.

The compounds of formula (II) which can be produced by the process of this invention include many compounds useful in such fields as pharmaceuticals and agricultural chemicals. Typical examples of such useful compounds are ibuprofen, naproxen, and alpha-[4-(1-oxo-2-isoindolinyl)phenyl]propionic acid (anti-inflammatory agent, indoprofen). Typical examples also include alpha-(2-thienyl)propionic acid, methyl alpha-(4-acetylaminophenyl)propionate, alpha-[4-(tert-butyl)-phenyl]isovaleric acid, methyl alpha-(4-alkoxyphenyl)-isovalerates, alpha-(4-biphenyl)propionic acid, methylalpha-(4-difluoromethoxyphenyl)isovalerate, and methylalpha-(4-alkoxyphenyl)propionates which are known as important synthetic intermediates for anti-inflammatory agents, and insecticides.

EXAMPLE 1

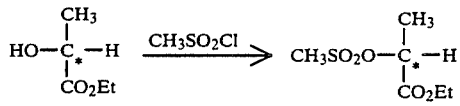

24.11 G (0.2041 mol) of ethyl L-(+)-lactate and 50 ml of anydrous pyridine were stirred in an ice bath. 17.0 Ml (25.2 g, 0.220 mol) of methanesulfonyl chloride was added dropwise over a period of 20 minutes, and the mixture was stirred for 1 hour at the same temperature and for 1 hour at room temperature. 200 Ml of water was added, and extraction was performed with methylene chloride (50 ml, 3 times). The extract was washed with water (50 ml), then dried with anhydrous magnesium sulfate, and vacuum concentrated. The red-colored oily residue was vacuum distilled, and 32.20 g of ethyl (−)-2-methanesulfonyloxypropionate was obtained in the form of a colorless liquid with bp 97°–102° C./2 Torr. Yield 82.0%.

$[\alpha]_D^{22}$ −50.55° (C=1.00, CHCL$_3$).

NMR(CDCl$_3$): δ1.30(3H, t, J=7 Hz), 1.59(3H, d, J=7 Hz), 3.11(3H, s), 4.23 (2H, q, J=7 Hz), 5.07.

As C$_6$H$_{12}$O$_5$S: (1H, q, J=7 Hz). Calculated values: C, 36.72; H, 6.17; S, 16.34%. Measured values: C, 36.54; H, 5.99; S, 16.59%.

EXAMPLE 2

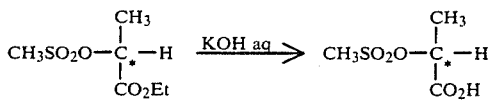

5.02 G (89.5 mmol) of potassium hydroxide was dissolved in 50 ml of water and stirred at 10°–20° C. 14.46 G (73.70 mmol) of the ethyl (−)-2-methanesulfonyloxypropionate obtained in Example 1 was added to this, and the mixture was stirred at the same temperature for 5 hours. Concentrated hydrochloric acid was added to bring the pH below 1, and extraction was performed with ethyl acetate (30 ml, 3 times). Anhydrous sodium sulfate and anhydrous magnesium sulfate were added in sequence to dry the extract, which was then vacuum concentrated, and 11.83 g of (−)-2-methanesulfonyloxypropionic acid was obtained in the form of crystals of mp 65°–72° C. Yield 95.4%.

$[\alpha]_D^{22}$ −49.81° (C=1.00, CHCl$_3$).

IR(KBr): 3025, 1748, 1360, 1178, 952, 840, 832, 528 cm$^{-1}$.

NMR(CDCl$_3$): δ1.67(3H, d, J=7 Hz), 3.19(3H, s), 5.17(1H, q, J=7 Hz), 9.78(1H, s).

As C$_4$H$_8$O$_5$S: Calculated values: C, 28.57; H, 4.78; S, 19.07%. Measured values: C, 28.58; H, 4.79; S, 18.91%.

EXAMPLE 3

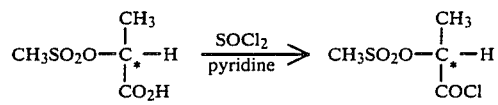

3.36 G (20.0 mmol) of the (−)-2-methanesulfonyloxypropionic acid obtained in Example 2 and 2.9 ml (4.8 g, 40 mmol) of thionyl chloride were mixed at room temperature. Then 3 drops of anhydrous pyridine were added, and the mixture was heated for 3 hours at 80°–90° C. The excessive thionyl chloride was removed by distillation under a vacuum (15 Torr) at a bath temperature of 80° C. Next vacuum distillation was performed, and 3.16 g of (−)-chloride-2-methanesulfonyloxypropionyl was obtained in the form of a colorless liquid of dp 70°–74° C./1.5 Torr. Yield 84.6%.

$[\alpha]^{22}$ −53.30° (=1, neat).

NMR(CDCl$_3$): 1.67(3H, d, J=7 Hz), 3.14(3H, s), 5.17(1H, q, J=7 Hz).

As C$_4$H$_7$ClO$_4$S: Calculated values: C, 25.74; H, 3.78; S, 17.18%. Measured values: C, 25.77; H, 3.89; S, 17.43%.

EXAMPLE 4

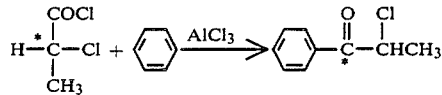

2.54 G (20.0 mmol) of R-(+)-chloride-2-chloropropionyl [S.-C. J. Fu, S. M. Birnbaum and J. P. Greenstein, J. Am. Chem. Soc., 76, 6054 (1954) and 7 ml of benzene were stirred in an ice bath. 3.00 G (22.5 mmol) of anhydrous aluminum chloride was added to this in small amounts, over a period of approximately 15 minutes, so that the reaction temperature would not exceed 10° C. The mixture was stirred for 20 minutes at the same temperature and for 1 hour at room temperature. The 30 ml of water was added under ice cooling so that the temperature of the reaction mixture would not exceed 25° C. 5 Ml of concentrated hydrochloric acid was added; ether extraction (50 ml, 2 times) was performed; and the extract was washed with water (30 ml, 2 times). The extract was dried with anhydrous magnesium sulfate and then vacuum concentrated. The oily residue was vacuum distilled, and 2.91 g of (−)-2-chloro-1-phenyl-1-propanone was obtained in the form of a colorless liquid of bp 110°–110° C./10 Torr. Yield 86.3%.

$[\alpha]_D^{20} -15.26°$ (C=1.00, CHCl$_3$).

NMR(CCl$_4$): δ1.68(3H, d, J=6H), 5.07(1H, q, J=6 H), 7.3 7.6(3H, m), 7.9~8.1(2H, m).

This was found to be optically pure from its NMR spectrum using an optically active shifting agent [Eu(TFC)] in carbon tetrachloride.

As C$_9$H$_9$IO: Calculated values: C, 64.10; H, 5.38 S, 21.03%. Measured values: C, 64.00; H, 5.48 S, 20.96%.

EXAMPLE 5

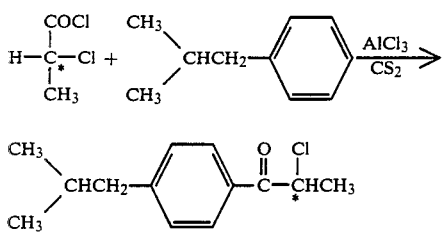

206 Mg (1.62 mmol) of R-(+)-chloride-2-chloropropionyl and 25% mg (1.92 mmol) of isobutylbenzene were dissolved in 1 ml of carbon disulfide and stirred at −20° to −25° C. 213 Mg (1.60 mmol) of anhydrous aluminum chloride was added over a period of 10 minutes, and the mixture was stirred for 10 minutes at the same temperature and for 30 minutes at −10° C. The 10 ml of water was added while cooling, followed by 2 ml of concentrated hydrochloric acid. Then ether extraction (20 ml, 2 times) was performed. The extract was washed with water (10 ml, 2 times), dried with anhydrous magnesium sulfate, and vacuum concentrated. The residue was purified by means of column chormatography (silica gel, methylene chloride), and 310 mg of (−)-2-chloro-1-(4-isobuitylphenyl)-1-propanone was obtained in the form of colorless crystals of mp 79° C. Yield 86.2%.

$[\alpha]_D^{20} -29.08°$ (C=1.00, CHCl$_3$).

IR(KB): 2950, 1685, 1605, 1265, 1188, 957, 645 cm$^{-1}$.

EXAMPLE 6

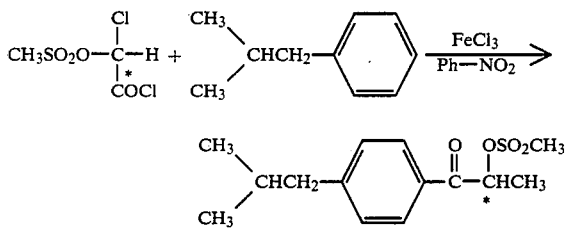

1.196 G (6.408 mmol) of (−)-chloride-2-methanesulfonyl-oxypropionyl and 1.290 g (9.612 mmol) of isobutylbenzene were dissolved in 3 ml of anhydrous nitrobenzene and stirred with ice cooling. Then 1.416 g (8.729 mmol) of anhydrous ferric chloride was added in small amounts over a period of 10 minutes. Then the mixture was stirred at room temperature for 9 hours. 20 Ml of water was added; ether extraction (20 ml, 3 times) was performed; and the extract was washed with water (20 ml, 3 times). Then the extract was dried with anhydrous magnesium sulfate and vacuum concentrated. The residue was separated by means of column chromatography (silica gel, methylene chloride), and 1.231 g of the coarse product was obtained. When it was analyzed by gas chromatography, it was learned as a result that it contained the target substance with a concentration of approximately 95%. When it was recrystallized from hexane, 1.005 g of (−)-2-methanesulfonyl-oxyl-(4-isobutylphenyl)-1-propanone was obtained in the form of colorless, needle-like crystals of mp 81°-82° C. Yield 55.1%.

$[\alpha]_D^{24} -52.48°$(C=1.00, CHCl).

IR(KBr): 2960, 1697, 1609, 1367, 1240, 1180, 1023, 930, 821, 745, 525 cm$^{-1}$.

NMR(CDCl$_3$): δ0.93(6H, d, J=7 Hz), 1.5 2.1(1H, m), 1.65(3H, d, J=7 Hz), 2.54(2H, d, J=7 Hz), 3.12(3H, s), 6.03(1H, q, J=7 Hz), 7.27(2H, d, J=9 Hz), 7.87(2H, d, J=9 Hz).

EXAMPLE 7

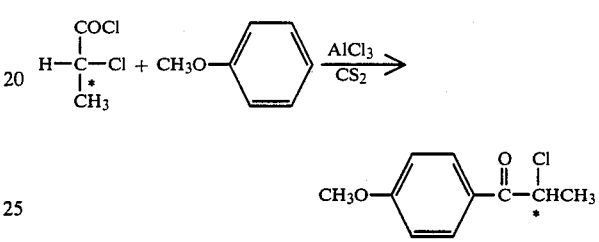

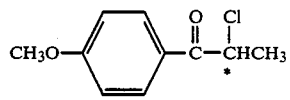

0.80 G (6.3 mmol) of R-(+)-chloride-2-chloropropionyl and 0.81 g (7.5 mmol) of anisole were dissolved in 4 ml of carbon disulfide and stirred at −20° to −25° C. 1.00 G (7.50 mmol) of anhydrous ammonium chloride was added to this, and the mixture was stirred for 10 minutes at the same temperature, and then for 1 hour at a temperature of −10° C. to −5° C. The reaction mixture was poured into about 2 ml of ice water, and ether extraction (15 ml, 2 times) was carried out. The extract was washed with water (10 ml, 2 times), dried with anhydrous magnesium sulfate, and then vacuum concentrated. The oily residue was purified by means of column chromatography (silica gel, ethyl acetate and hexane), and (−)-2-chloro-1-methoxyphenyl)-1-propanone was obtained in the form of a colorless oily substance.

$[\alpha]_D^{20} -50.2°$(C=0.84, CHC$_3$).

IR(neat): 1690, 1605, 1515, 1260, 1173, 1032, 958, 847 cm$^{-1}$.

NMR(CDCl): δ1.70(3H, d, J=6 Hz), 3.82(3H, s), 5.15(1H, q, J=6 Hz), 6.90(2H, d, J=9 Hz), 7.84(2H, d, J=9 Hz).

EXAMPLE 8

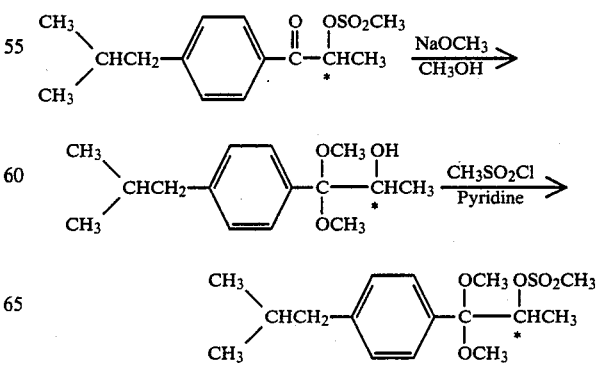

36 Mg of metallic sodium (1.6 mg-atom) was dissolved in 3 ml of anhydrous methanol and stirred under ice cooling. 284 Mg (1.00 mmol) of (−)-2-methanesulfonyloxy-1(4-isobutyl-phenyl)-1-propanone obtained in Example 6 was added, and the mixture was stirred for 10 minutes at the same temperature and then for 4 hours at room temperature. 10 Ml of water was added, and extraction was performed with methylene chloride (5 ml, 3 times). Two drops of pyridine were added to the extract, and it was dried with anhydrous magnesium sulfate and then vacuum concentrated. The oily residue was dissolved in 1 ml of anhydrous pyridine and stirred at room temperature. Then 0.12 ml (178 mg, 1.6 mmol) of methanesulfonyl chloride was added, and the mixture was stirred for 1.5 hours at room temperature. 10 Ml of water was added, and extraction was performed with methylene chloride (10 ml, 3 times). The extract was dried with anhydrous magnesium sulfate and then vacuum concentrated. The oil residue was purified by means of column chromatography (silica gel, methylene chloride), and 283 mg of (+)-2-methanesulfonyloxy-1-(4-isobutylphenyl)-1-propanone dimethyl acetal was obtained in the form of an anhydrous oily substance. Yield 85.6%.

$[\alpha]_D^{25} + 12.1°(C = 1.00, CHCl_3)$.

NMR(CDCL$_3$): δ0.88(6H, d, J=7 Hz), 1.16(3H, d, J=7 Hz), 1.6 2.1(1H, m), 2.44(2H, d, J=7 Hz), 3.06(3H, s), 3.18(3H, s), 3.26(3H, s), 4.95(1H, q, J=7 Hz), 7.10(2H, d, J=8 Hz), 7.32(2H, d, J=8 Hz).

EXAMPLE 9

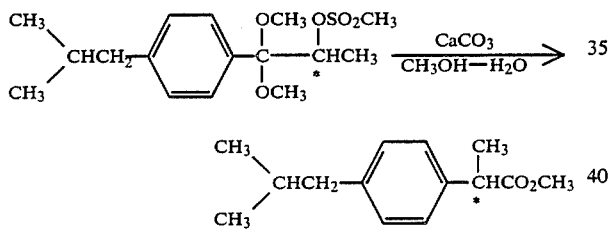

283 Mg (0.857 mmol) of (+)-2-methanesulfonyloxy-1-(4-isobutylphenyl)-1-propanone dimethyl acetal obtained in Example 8 and 100 mg (1.00 mmol) of calcium carbonate were subjected to heating and reflux for 63 hours in 7 ml of a mixed solvent of water and methanol (ratio 3:7 by weight). 40 Ml of water was added, and extraction was performed with methylene chloride (15 ml, 3 times). The extract was dried with anhydrous magnesium sulfate and then vacuum concentrated. The oily residue was purified by means of column chormatography (silica gel, methylene chloride), and 142 mg of ethyl (−)-alpha-(4-isobutylphenyl)propionate was obtained in the form of a colorless oily substance. Yield 75.2%.

The NMR of that material agreed with that of an authentic sample of the dl form.

$[\alpha]_D^{23} - 56.2°(C = 1.00, CHCl_3)$.

EXAMPLE 10

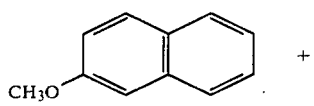

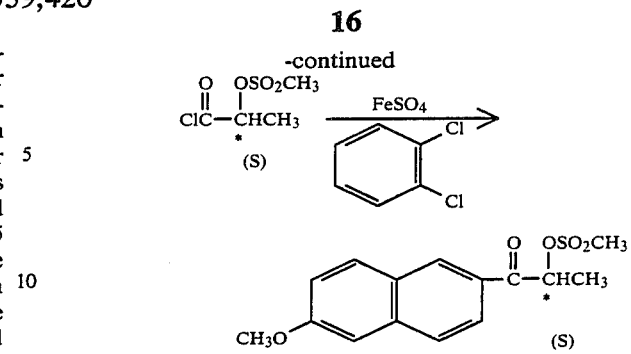

791 Mg (5.00 mmols) of β-methoxynaphthalene and 933 mg (5.00 mmols) of (S)-2-(methylsulfonyloxy)propionyl chloride were dissolved in 5 ml of anhydrous o-dichlorobenzene, followed by stirring at room temperature. To the solution was added 296 mg of dry ferric sulfate obtained by drying ferric sulfate heptahydrate at 150° C. for 3 hours in vacuo, and the mixture was stirred at 70° C. for 18 hours under an argon gas stream. 30 Ml of water was added to the mixture, which was then extracted with methylene chloride (30 ml×2). The extract was washed with water (10 ml×2), dried over anhydrous magnesium sulfate and concentrated under reduced pressure. The oily residue was purified by column chromatography (silica gel, methylene chloride) to obtain (S)-1-(6-methoxy-2-naphthyl-2-methylsulfonyloxy-1-propanone as a colorless glass-like material having $[\alpha]_D^{26} - 35.6°(c = 0.982, CHCl_3)$. The resulting product was crystallized in methanol and recrystallized from the same solvent to obtain colorless needles having a melting point of 156°–157° C.

$[\alpha]_D^{26} - 36.0° (c = 0.806, CHCl_3)$.

IR (KBr): 1697, 1629. 1490, 1370, 1280, 1196, 1175, 1020, 938, 900, 823, 527 cm$^{-1}$.

NMR (CDCl): δ1.70 (3H, d, J=7 Hz), 3.13 (3H, s), 3.92 (3H, s), 6.16 (1H, q, J=7 Hz), 7.1–7.3 (2H, m), 8.37 (1H, broad s).

Elementary Analysis: Calcd for $C_{15}H_{16}O_5S$: C, 58.42; H, 5.23; S, 10.40% Found: C, 58.44; H, 5.12; S, 10.67%

EXAMPLE 11

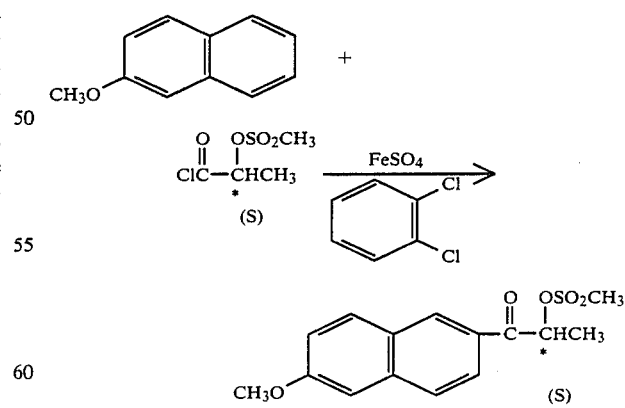

In the same manner as described in Example 10 but using β-methoxynaphthalene and (S)-2-(benzenesulfonyloxy)-propionyl chloride, (S)-1-(6-methoxy-2-naphthyl)-2-benzenesulfonyloxy-1-propanone was obtained as colorless crystals.

Melting point: 74°–75° C.

$[\alpha]_D^{20} + 35.1°$ (C=1.30, CHCl$_3$).

IR (KBr): 1702, 1628, 1350, 1275, 1197, 1180, 1020, 934, 910, 899, 758, 623 cm$^{-1}$.

NMR (CDCl$_3$): δ1.65 (3H, d, J=7H), 3.93 (3H, s), 5.94 (1H, q, J=7 Hz), 7.1-8.0 (10H, m), 8.33 (1H, broad s).

What is claimed is:

1. A process for preparing an optically active alpha-aromatic group substituted alkanoic acid on its ester of the general formula:

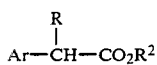  (II)

wherein Ar represents an aromatic group, R represents a saturated aliphatic group, R$^2$ represents a hydrogen atom, an alkyl group or a hydroxyalkyl group, and * indicates an asymmetric carbon atom, or a pharmaceutically acceptable salt thereof, which comprises contacting an optically active alkane acid halide of the general formula:

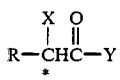

wherein X is a halogen atom or a sulfonyloxy group, Y is a halogen atom and R and * are as defined above, with an aromatic compound of the general formula:

wherein Ar is defined as above, in the presence of a Lewis acid, and rearranging the resulting 1-aromatic-group-substituted-1-alkanone to the corresponding alpha-aromatic-group-substituted alkanoic acid or its ester, and optionally converting a compound of formula II to its pharmaceutically acceptable salt.

2. The process of claim 1 wherein the reaction of the optically active alkane acid halide and the aromatic compound is carried out at a temperature of about −10° C. to 100° C.

3. The process of claim 1 wherein the reaction of the optically active alkane acid halide and the aromatic compound is carried out at a temperature of about 0° C. to 50° C.

4. The process of claim 1 wherein X is a sulfonyloxy group and the Lewis acid is a relatively weak Lewis acid.

5. The process of claim 4 wherein the Lewis acid is selected from the group consisting of ferric sulfate, ferric chloride, ferrous chloride, zinc chloride and magnesium bromide.

6. The process of claim 1 wherein X is a sulfonyloxy group of the general formula

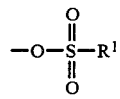

wherein R$^1$ is a substituted or unsubstituted alkyl or cycloalkyl group or an aromatic group.

7. The process of claim 6 wherein R$^1$ is lower alkyl, lower haloalkyl, a d- or l-10-camphoryl group, cycloalkyl or a group of the formula

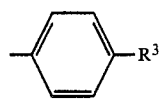

wherein R$^3$ is a hydrogen atom, a halogen atom, a nitro group or a lower alkyl group.

8. The process of claims 1, 2, 3, 4, 5, 6 or 7 wherein Ar is a 6-methoxy-2-naphthyl group and R is a methyl group.

* * * * *